United States Patent [19]

Figdor et al.

[11] Patent Number: 4,939,081

[45] Date of Patent: Jul. 3, 1990

[54] CELL-SEPARATION

[75] Inventors: Carl G. Figdor, Hertogenbosch; Peter Sloot, Aerdenhout, both of Netherlands

[73] Assignee: The Netherlands Cancer Institute, Amsterdam, Netherlands

[21] Appl. No.: 54,436

[22] Filed: May 27, 1987

[51] Int. Cl.$^5$ .................... A01N 1/02; G01N 21/00
[52] U.S. Cl. ........................ 435/2; 209/148;
209/576; 209/579; 356/72; 356/337; 356/339;
356/340; 356/342; 356/343; 424/529; 424/533;
424/534; 435/29; 435/30; 435/34; 436/63;
436/164
[58] Field of Search ................. 435/29, 30, 34, 2;
436/63, 164; 356/72, 337, 340, 343; 209/579

[56] References Cited

U.S. PATENT DOCUMENTS

| 3,770,351 | 11/1973 | Wyatt | 356/343 |
|---|---|---|---|
| 3,785,735 | 1/1974 | Friedman et al. | 356/343 |
| 4,280,623 | 7/1981 | Legorreta | 356/72 |
| 4,487,700 | 12/1984 | Kanter | 436/63 |
| 4,599,307 | 7/1986 | Saunders | 436/63 |
| 4,747,686 | 5/1981 | Sato | 356/72 |

OTHER PUBLICATIONS

Figdor et al.–J. Immunol. Method–vol. 40 (1981), pp. 275–288.
Lindahl–Nature–vol. 161 (1948).
Pretlow et al.–Cell Biophysics, vol. 1, (1979), pp. 195–210.
Mulder et al.–J. Immunol. Methods, vol. 47 (1981), pp. 31–38.

*Primary Examiner*—Sam Rosen
*Attorney, Agent, or Firm*—Rosen, Dainow & Jacobs

[57] ABSTRACT

A method and apparatus for separating particles by means of a contra-flow centrifuge, wherein a monitor system is used to analyze or control the separation process. The monitor system used impinges a monochromatic light beam on a sample of the separated particles, and measures the light scattering not only in the beam-forward direction, but also in the beam-reverse and beam-lateral directions. This reduces the processing time and increases the reliabiity of output data.

7 Claims, 1 Drawing Sheet

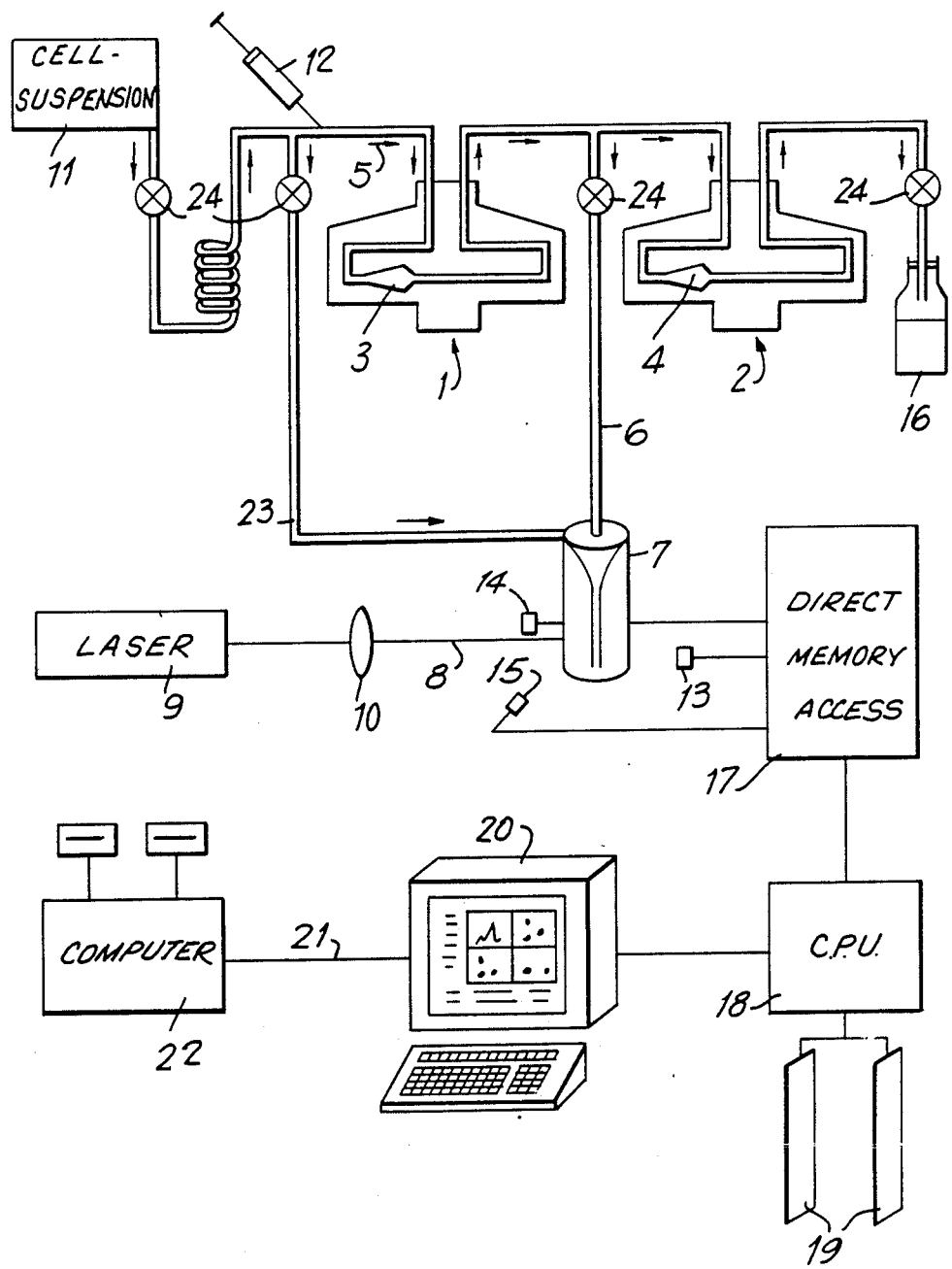

CELL-SEPARATION

The invention relates to a method of separating blood and bone-marrow cells on the basis of specific mass and volume with the aid of an elutriation rotor and monitor system coupled to the output thereof, in which through the scattering of a light beam on the cells of a part of the separated fraction this fraction is tested for the quantitative presence of cells having particular cell properties, and in which on the basis of elutriator data parameters of rate-of-flow and the rotational speed are controlled during the process. The light is derived from a monochromatic light-source, for example a laser. The measurement performed on the cells is achieved in a non-destructive manner and not by initially colour-staining the concerned cells.

There is a great need for the separation of inhomogeneous cell populations for both clinical and scientific purposes.

The separation of cells with the aid of an elutriator, that is to say a contra-flow centrifuge, is described in "Cell Biophysics" I (1979) pages 195 to 210 for example.

The separation is achieved on the basis of the difference in sedimentation-rate of the cells. The cell suspension is fed to a chamber the walls of which diverge over a certain length thereof and which converge again toward the exit from the chamber. The chamber forms part of a rotor and such that the contents of the chamber are subjected to centrifugal force opposite to the direction in which the suspension flows through the chamber. The separation of the cells is achieved by setting the elutriator parameters of rate-of-flow and rotational speed accordingly and such that a dynamic equilibrium prevails in the chamber whereby cell arrangement takes place on the basis of their sedimentation rate. By either reducing the rotational speed or by increasing the rate-of-flow thereafter, the various cell fractions can be separated.

Two problems arise essentially in a method of separation such as this:

1. In the setting of the elutriator parameters in order to obtain optimal separation, this setting is for example dependent on the temperature, the concentration, difference in the cells to be separated etc. This means that the setting must be made on the basis of laborious trial-and-error methods.

2. In order to obtain an insight into the distribution of cells in a fraction with respect to their cell properties such as size, optical density and morphology, it is necessary to analyze these fractions. This occurs retrospectively and in which a number of cells, 300 from a fraction for example, are examined. Information obtained from such an examination is only available after a relatively long time, 4 hours for example and is somewhat unreliable due to the small number of cells examined. Added to which correction of the separation process is no longer possible on the basis of this information.

In the "Journal of immunological methods" 47 (1981) pages 31 to 38, there is described how, with relation to the cell property of 'size', cells flowing from an elutriator can be identified in a non-destructive manner via an on-line detection system and how the separating process can be controlled on the basis of this data.

Identification on the basis of the size of the cells according to the described method is achieved by irradiating these with a laser beam and then by measuring the scattering of the light in the direction of the beam, the intensity of this so-called 'forward scattering' thus gives direct information of the size of the cells over which the light has been scattered.

The present invention relates to a method in which is made of a separation-technique with the aid of an elutriator in which the elutriator parameters can be optimally set during the separation process and in which the separated fractions can be continuously analyzed at the same time during the separation process not only with respect to cell size but also with relation to other cell properties of importance such as specific density, morphology etc.

The term 'optimal setting' as used herein is to be construed as meaning: That which leads to such fractionation that in the cell population of a fraction, an optimum number of cells are present with a particular cell property of a particular value and lying within a particular range of values.

The method according to the invention is characterised by the fact that the intensity of the scattered light is measured multi-directionally and simultaneously and namely in the direction of the light beam, in the reverse direction and in a direction perpendicular thereto so that data, concerning the degree to which cells having specific properties corresponding to each of the directions to be measured, become available during the separation process for controlling and/or analysis purposes.

Thus the intensity of the scattering is measured simultaneously in each of these directions during the separation process.

Each of these directions provides data concerning a particular property. That is to say the cell size in the direction of the beam, the so-called 'forward scatter'; the density of the core in the reverse direction, the so-called 'back-scatter'; and the internal structure of the cell in the lateral direction, the so-called 'side-scatter'. Thus in the course of the separation continuous and simultaneous data can be obtained on the three quoted cell properties, and also during the course of the separation process action can be taken in setting the elutriator parameters on the basis of this data.

It is evident that the method according to the invention will lead to an enormous saving in time due to the considerably larger number of cells involved in measurement. When compared to 'retrospective analysis' the data now obtained is also reliable.

The method according to the invention is also applicable to the separation and analysis of particles other than blood components and such as particles of asbestos in water and suchlike.

According to one embodiment of the method according to the invention, still further data can be obtained concerning the cell properties during the course of the separation process and which can also be used for controlling and/or analysis purposes and which may be data concerning the fluidity of the cell membranes arising directly from the polarising action of the cells. This embodiment is characterized by the fact that at the same time the polarising or depolarising actions of the cells or cell components on the light beam are measured by detecting the scattered light via polarising optical elements and /or to polarise the light falling thereon.

In a preferred embodiment of the method according to the invention, the quoted data is displayed on a CRT monitor and on which the number of cells per fraction can be shown as a function of the concerned cell property, other features being shown multidimensionally.

According to another embodiment of the method according to the invention, by feeding back the signals corresponding to the three scattering directions from the detectors to the setting mechanism for the elutriation-parameters, these parameters will be continuously and automatically set to their optimal values.

Furthermore, the invention includes an apparatus for carrying out the method quoted herefor and which apparatus comprises an elutriator rotor at the output of which there is located a measuring-instrument in which the cells are irradiated one-by-one, a light source the focussed beam of which is directed to the cells in the measuring-instrument and around which measuring-instrument at least three detectors are arranged for measuring the scattered radiation, two of which are arranged in the direction of the beam, one of which is arranged in front of and one of which is arranged in a direction perpendicular to the beam alongside the measuring instrument. A cuvette is preferably used as a measuring-instrument and hydro-focussing in order to make irradiation of the cells possible one-by-one. Naturally, it is possible to measure the radiations in both the forward and backward directions also with detectors which are located to the sides of the beam so that then combinations components in both said directions together with a side-scatter-component are measured.

When both control and/or analysis functions are to be carried out at the same time with respect to the fluidity of the cell membrane for example, and through which the polarising actions of the cells are to be measured, an embodiment of an apparatus according to the invention therefor is characterized by the fact that between the measuring-instrument and each of the detectors there is provided a polarising optical-element and/or there is provided a like element located at the light beam falling on the measuring-instrument.

In a further preferred embodiment of the apparatus, the output signals from the detectors are fed to the CRT monitor via a data-acquisition system. When the data-acquisition system includes a multi-dimensional memory which is connected to the CRT monitor, the contents of the memory can be displayed on the monitor.

In yet an even further preferred embodiment of the apparatus according to the invention, the output signals are directly fed back to the elutriator—setting mechanism in order to control the elutriator-parameters.

The invention will now be described further with reference t the accompanying drawing which illustrates schematically an embodiment of an apparatus according to the invention and with the aid of which the method according to the invention can be carried out.

The drawing shows two elutriators 1 and 2 connected in series and each provided with an elutriator-chamber 3 and 4. The direction-of-flow of the supply of cell-suspension, comprising a medium 11, to which at 12 a cell suspension is added, is indicated by the arrows 5. The second rotor serves to achieve a better cell concentration in the final fractions to be received in the vessel 16. Fractionation is achieved by reducing the rotational speed of the first rotor step-by-step. In order to analyse the suspension flowing from rotor 1, a small portion of this is tapped-off by means of a line 6 and fed to a cuvette 7 wherein it is 'focussed' in such a manner by hydro-focussing that each cell is irradiated separately by the light beam 8 falling thereon and which light beam is produced by a laser 9 and thereafter by a lens-system 10 focussing the light beam on the concerned place in the cuvette 7.

The light in the cuvette 7 scattered by the cells therein is detected by the detector 13 (the 'forward-scatter'), the detector 14 (the 'back-scatter') and the detector 15 (the 'side-scatter'). Optimal detection of the scattered light is obtained by the chosen geometrical-disposition of the detectors and their distance from the cells and in such a manner that, measured with respect to the axis of the laser beam, the top-angle of the detected beam for the detectors 13, 14 and 15 subtends angles of approximately 1° to 7°; from approximately 75° to 100° and approximately 160° to 180° respectively.

On the basis of the scattered light received from each of the passing cells in each of the detectors 13, 14 and 15, the signals generated in the detectors in response to the light received are fed to an on-line data-acquisition system (17 to 20 inclusive). Via a Direct Memory Access 17 herein, thus exterior to a Central Processor Unit - C.P.U. the three digitalised paramaters are cumulatively stored in a memory 19 with a frequency of several thousand, for example 5000, cells per second. The C.P.U. is provided with a specially developed operating system O.S. that makes it possible, in a user-compatible and simple-to-operate manner, to display the content of the memory 19 after subjection to a specific process on the CRT monitor 20 with the aid of a set of graphic routines. Alongside of this possibility there is also the possibility, with the aid if an O.S. implemented local network, to extract the complete data from the memory 19 and transmit it to a host-computer 22 for further statistical analysis via a series-connected co-axial cable 21.

The statistical analysis itself can also be recorded in the O.S. and through which the 4-dimensional memory can be split up in clusters, assuming multi-dimensional normal distributions, and after which unique determination of the statistical parameters of the various populations follows. Following this, a specially purpose developed iterating-process ensures optimal characterisation of the (sub)populations present in the fraction.

With the aid of polarising filters interposed in the ingoing beam and/or alongside the detectors, between detectors and the cuvette, it is possible to obtain even more detailed data concerning the properties of the separated cells without (bio)chemical manipulation taking place. After analysis this data provides, for example, information concerning membrane properties of the cells (fluidity) and the internal structure.

An exemplary embodiment of the method according to the invention aided by apparatus as described with reference to the drawing.

Human blood-cells, prepared from 500 ml of human peripheral blood pretreated with the aid of a blood-component separator (see 'Journal of Immunological Methods' 40 (1981) pages 275 to 288), were suspended in a buffer-solution medium and introduced into the rotor 1. Centrifugal elutriation takes place after introduction into the rotor of approximately $700 \cdot 10^6$ leucocytes and approximately $1200 \cdot 10^6$ erythrocytes with a flow-rate of 12 ml per minute. After the flow-rate was increased to 18 ml per minute, the cells were fractionated by reducing the rotational speed of the rotor step-by-step from approximately 3800 revolutions per minute down to approximately 1000 revolutions per minute. The rotor 2 was maintained running at a constant speed of 4500 revolutions per minute. This fractionation resulted in the production of a number of fractions, the enriched quantities of respectively, erythrocytes, lymphocytes (and subpopulations thereof), monocytes, neutrophilic-eosinophilic-and-basophilic granulocytes comprising: (see accompanying table). During elutriation, a by-pass flow of approximately 0.1 ml per minute was tapped-off and hydrofocussed in the cuvette (7) with the aid of the sheathing liquid (11) producing sheath-flow, and after which excitation took place by using a focussed Ne-Ne laser beam with a wavelength of 632.8 nanometers. The detected signals were processed and displayed on-line on the CRT monitor giving direct information concerning the cells leaving the rotor at moment. Via a stepping-motor, this information was used to set the rotor revolutions such that optimal separation was obtained. This information was used firstly to determine the moment at which another number of revolutions was to be set and to determine the numerical value of the number of revolutions per minute to be set (see accompanying table). Following hereon the memory content was 'read-out' by a host computer and then processed in a specific statistical manner through which, and without intervention by an operator, the (sub)populations of the fractions so obtained were differentiated into different cell distributions of which the blood is composed. Likewise, the number of cells in each distribution was determined. The results obtained using this exemplary embodiment ar given in the table.

TABLE

Statistics of a centrifugal elutriation experiment-6H of 700 × $10^6$ mononuclear cell with an elutriation times of approximately 8 min/fraction and a flow rate of 18 ml/min

| Fraction | Rotor speed (rpm) | Total number of cells (× $10^6$) | Percentage of cells in fraction | | | |
|---|---|---|---|---|---|---|
| | | | E | L | M | G |
| 1 | 3500 | 115 | 90 | 10 | | |
| 2 | 3300 | 60 | 50 | 50 | | |
| 3 | 3100 | 225 | 20 | 80 | | |
| 4 | 3000 | 25 | 15 | 80 | 5 | |
| 5 | 2900 | 8 | 3 | 57 | 35 | 5 |
| 6 | 2900 | 7 | 3 | 20 | 72 | 5 |
| 7 | 2800 | 75 | 3 | 5 | 90 | 2 |
| 8 | 2700 | 35 | 3 | 4 | 86 | 7 |
| 9 | 2650 | 50 | 3 | 11 | 47 | 39 |
| 10 | STOP | 100 | 3 | 4 | 11 | 82 |

| Fraction | Number of cells in fraction (× $10^6$) | | | | Average number of cells per minute (× $10^6$) | | | |
|---|---|---|---|---|---|---|---|---|
| | E | L | M | G | E | L | M | G |
| 1 | 103.5 | 11.5 | | | 12.9 | 1.5 | | |
| 2 | 30 | 30 | | | 3.8 | 3.8 | | |
| 3 | 45 | 180 | | | 5.6 | 22.5 | | |
| 4 | 3.8 | 20 | 1.3 | | | 2.5 | 0.2 | |
| 5 | 0.2 | 4.5 | 2.6 | 0.5 | 0.6 | 0.5 | 0.3 | 0.1 |
| 6 | 0.2 | 1.4 | 5.3 | 0.4 | 0.5 | 0.2 | 0.7 | 0.1 |
| 7 | 2.3 | 3.8 | 67.5 | 1.5 | 0.3 | 0.5 | 8.4 | 0.2 |
| 8 | 1.1 | 1.4 | 30.1 | 2.5 | 0.1 | 0.2 | 3.8 | 0.3 |
| 9 | 1.5 | 5.5 | 23.5 | 19.5 | 0.2 | 0.7 | 2.9 | 2.4 |
| 10 | 3 | 4 | 11 | 82 | 0.4 | 0.5 | 1.4 | 10.3 |

E, erythrocytes; L, lymphocytes; M, Monocytes; G, granulocytes.

What we claim is:

1. A method for separating blood and bone-marrow cells on the basis of specific mass and volume with the aid of an elutriation rotor and a monitor system coupled to the output thereof and in which on the basis of the scattering of a light beam on the cells of a part of the separated fraction this fraction is tested for the quantitative presence of cells having particular cell properties and on the basis of such tests elutriator parameters of rate-of-flow and rotational speed are controlled during the process, characterized in that the intensity of the scattered beam is measured three-dimensionally and simultaneously in the direction of the light beam, in the reverse direction and in a direction perpendicular thereto so that data concerning the degree to which cells having specific properties corresponding to each of the directions to be measured becomes available during the separation process, and that date is used during the separation process to control elutriator parameters to improve the cell separation.

2. A method as claimed in claim 1 in which at the same time the polarising or depolarising actions of the cells or cell components on the light beam are measured by detecting the scattered light via polarising optical elements or by polarising the light falling on the cells.

3. A method as claimed in claim 1 or claim 2 in which the quantitative date arising from the separating process is continuously displayed on a CRT monitor.

4. A method as claimed in claim 1 or claim 2 in which the quantitive data obtained is fed back to the elutriator mechanism in such a manner that the elutriator parameters obtained with respect to a required fraction automatically effect optimal setting.

5. A method for improving the separation of particular desired particles having specific mass and volume in an elutriation process using a non-destructive technique, comprising the steps:
 (a) subjecting a suspension of the particles to be separated to an elutriation process,
 (b) subjecting a fraction of the elutriated particles to a non-destructive monitoring process by impinging a monochromatic light beam on the particle fraction causing scattering of the light beam in various directions, said light beam having characteristics that cause scattering by said particular particles,
 (c) measuring the scattering light intensity in the forward direction of the beam, in the reverse direction opposite to the beam direction, and in a direction perpendicular to the beam direction,
 (d) using the measurement of step (c) to control operation of the elutriation process to improve the separation of said particular particles.

6. The method of claim 5, wherein the impinging light beam is polarized.

7. The method of claim 5, wherein the intensity of the scattered light is measured through a polarizing element.

* * * * *